US010052065B2

(12) United States Patent
Boesen (10) Patent No.: US 10,052,065 B2
(45) Date of Patent: Aug. 21, 2018

(54) EARPIECE LIFE MONITOR WITH CAPABILITY OF AUTOMATIC NOTIFICATION SYSTEM AND METHOD

(71) Applicant: BRAGI GmbH, München (DE)

(72) Inventor: Peter Vincent Boesen, München (DE)

(*) Notice: Subject to any disclaimer, the term of this patent is extended or adjusted under 35 U.S.C. 154(b) by 0 days.

(21) Appl. No.: 15/463,462

(22) Filed: Mar. 20, 2017

(65) Prior Publication Data

US 2017/0273622 A1 Sep. 28, 2017

Related U.S. Application Data

(60) Provisional application No. 62/312,139, filed on Mar. 23, 2016.

(51) Int. Cl.
| | |
|---|---|
| *H04R 25/00* | (2006.01) |
| *A61B 5/00* | (2006.01) |
| *H04R 1/10* | (2006.01) |
| *G10L 13/00* | (2006.01) |
| *G08B 25/01* | (2006.01) |
| *G08B 25/10* | (2006.01) |
| *G08B 21/02* | (2006.01) |

(52) U.S. Cl.
CPC .......... *A61B 5/6803* (2013.01); *A61B 5/0015* (2013.01); *A61B 5/742* (2013.01); *A61B 5/746* (2013.01); *G08B 25/016* (2013.01); *G08B 25/10* (2013.01); *G10L 13/00* (2013.01); *H04R 1/1016* (2013.01); *H04R 1/1041* (2013.01); *G08B 21/02* (2013.01); *H04R 2201/107* (2013.01); *H04R 2420/07* (2013.01)

(58) Field of Classification Search
CPC ..... H04R 5/033; H04M 1/6058; H04W 4/008
USPC .................................................... 381/315, 74
See application file for complete search history.

(56) References Cited

U.S. PATENT DOCUMENTS

| | | |
|---|---|---|
| 3,934,100 A | 1/1976 | Harada |
| 4,150,262 A | 4/1979 | Ono |
| 4,334,315 A | 6/1982 | Ono et al. |

(Continued)

FOREIGN PATENT DOCUMENTS

| | | |
|---|---|---|
| EP | 1017252 A2 | 7/2000 |
| GB | 2074817 | 4/1981 |

(Continued)

OTHER PUBLICATIONS

Announcing the $3,333,333 Stretch Goal (Feb. 24, 2014).

(Continued)

*Primary Examiner* — Alexander Jamal
(74) *Attorney, Agent, or Firm* — Goodhue, Coleman & Owens, P.C.

(57) ABSTRACT

An earpiece includes an earpiece housing, at least one biometric sensor disposed within the earpiece, a wireless transceiver disposed within the earpiece for voice communications, an intelligent control operatively connected to the at least one biometric sensor and the wireless transceiver, a speaker operatively connected to the intelligent control, and at least one microphone operatively connected to the intelligent control. The earpiece is configured to monitor biometrics of a user using the at least one biometric sensor, communicate biometric data to the user, detect a crisis level event, and communicate occurrence of the crisis level event using the wireless transceiver.

17 Claims, 5 Drawing Sheets

(56) References Cited

U.S. PATENT DOCUMENTS

| | | |
|---|---|---|
| 4,375,016 A | 2/1983 | Harada |
| 4,588,867 A | 5/1986 | Konomi |
| 4,654,883 A | 3/1987 | Iwata |
| 4,682,180 A | 7/1987 | Gans |
| 4,791,673 A | 12/1988 | Schreiber |
| 4,865,044 A | 9/1989 | Wallace et al. |
| 5,191,602 A | 3/1993 | Regen et al. |
| 5,201,007 A | 4/1993 | Ward et al. |
| 5,280,524 A | 1/1994 | Norris |
| 5,295,193 A | 3/1994 | Ono |
| 5,298,692 A | 3/1994 | Ikeda et al. |
| 5,343,532 A | 8/1994 | Shugart |
| 5,363,444 A | 11/1994 | Norris |
| 5,497,339 A | 3/1996 | Bernard |
| 5,606,621 A | 2/1997 | Reiter et al. |
| 5,613,222 A | 3/1997 | Guenther |
| 5,692,059 A | 11/1997 | Kruger |
| 5,721,783 A | 2/1998 | Anderson |
| 5,749,072 A | 5/1998 | Mazurkiewicz et al. |
| 5,771,438 A | 6/1998 | Palermo et al. |
| 5,802,167 A | 9/1998 | Hong |
| 5,929,774 A | 7/1999 | Charlton |
| 5,933,506 A | 8/1999 | Aoki et al. |
| 5,949,896 A | 9/1999 | Nageno et al. |
| 5,987,146 A | 11/1999 | Pluvinage et al. |
| 6,021,207 A | 2/2000 | Puthuff et al. |
| 6,054,989 A | 4/2000 | Robertson et al. |
| 6,081,724 A | 6/2000 | Wilson |
| 6,094,492 A | 7/2000 | Boesen |
| 6,111,569 A | 8/2000 | Brusky et al. |
| 6,112,103 A | 8/2000 | Puthuff |
| 6,157,727 A | 12/2000 | Rueda |
| 6,167,039 A | 12/2000 | Karlsson et al. |
| 6,181,801 B1 | 1/2001 | Puthuff et al. |
| 6,208,372 B1 | 3/2001 | Barraclough |
| 6,230,029 B1 | 5/2001 | Yegiazaryan et al. |
| 6,275,789 B1 | 8/2001 | Moser et al. |
| 6,339,754 B1 | 1/2002 | Flanagan et al. |
| 6,408,081 B1 | 6/2002 | Boesen |
| 6,424,820 B1 | 7/2002 | Burdick et al. |
| D464,039 S | 10/2002 | Boesen |
| 6,470,893 B1 | 10/2002 | Boesen |
| D468,299 S | 1/2003 | Boesen |
| D468,300 S | 1/2003 | Boesen |
| 6,542,721 B2 | 4/2003 | Boesen |
| 6,560,468 B1 | 5/2003 | Boesen |
| 6,654,721 B2 | 11/2003 | Handelman |
| 6,664,713 B2 | 12/2003 | Boesen |
| 6,694,180 B1 | 2/2004 | Boesen |
| 6,718,043 B1 | 4/2004 | Boesen |
| 6,738,485 B1 | 5/2004 | Boesen |
| 6,748,095 B1 | 6/2004 | Goss |
| 6,754,358 B1 | 6/2004 | Boesen et al. |
| 6,784,873 B1 | 8/2004 | Boesen et al. |
| 6,823,195 B1 | 11/2004 | Boesen |
| 6,852,084 B1 | 2/2005 | Boesen |
| 6,879,698 B2 | 4/2005 | Boesen |
| 6,892,082 B2 | 5/2005 | Boesen |
| 6,920,229 B2 | 7/2005 | Boesen |
| 6,952,483 B2 | 10/2005 | Boesen et al. |
| 6,987,986 B2 | 1/2006 | Boesen |
| 7,136,282 B1 | 11/2006 | Rebeske |
| 7,203,331 B2 | 4/2007 | Boesen |
| 7,209,569 B2 | 4/2007 | Boesen |
| 7,215,790 B2 | 5/2007 | Boesen et al. |
| 7,463,902 B2 | 12/2008 | Boesen |
| 7,508,411 B2 | 3/2009 | Boesen |
| 7,979,035 B2 | 7/2011 | Griffin et al. |
| 7,983,628 B2 | 7/2011 | Boesen |
| 8,095,188 B2 | 1/2012 | Shi |
| 8,140,357 B1 | 3/2012 | Boesen |
| 8,300,864 B2 | 10/2012 | Müllenborn et al. |
| 8,436,780 B2 | 5/2013 | Schantz et al. |
| 8,719,877 B2 | 5/2014 | VonDoenhoff et al. |
| 2001/0005197 A1 | 6/2001 | Mishra et al. |
| 2001/0027121 A1 | 10/2001 | Boesen |
| 2001/0056350 A1 | 12/2001 | Calderone et al. |
| 2002/0002413 A1 | 1/2002 | Tokue |
| 2002/0007510 A1 | 1/2002 | Mann |
| 2002/0010590 A1 | 1/2002 | Lee |
| 2002/0030637 A1 | 3/2002 | Mann |
| 2002/0046035 A1 | 4/2002 | Kitahara et al. |
| 2002/0057810 A1 | 5/2002 | Boesen |
| 2002/0076073 A1 | 6/2002 | Taenzer et al. |
| 2002/0118852 A1 | 8/2002 | Boesen |
| 2003/0065504 A1 | 4/2003 | Kraemer et al. |
| 2003/0100331 A1 | 5/2003 | Dress et al. |
| 2003/0104806 A1 | 6/2003 | Ruef et al. |
| 2003/0115068 A1 | 6/2003 | Boesen |
| 2003/0125096 A1 | 7/2003 | Boesen |
| 2003/0218064 A1 | 11/2003 | Conner et al. |
| 2004/0070564 A1 | 4/2004 | Dawson et al. |
| 2004/0160511 A1 | 8/2004 | Boesen |
| 2005/0043056 A1 | 2/2005 | Boesen |
| 2005/0125320 A1 | 6/2005 | Boesen |
| 2005/0148883 A1 | 7/2005 | Boesen |
| 2005/0165663 A1 | 7/2005 | Razumov |
| 2005/0196009 A1 | 9/2005 | Boesen |
| 2005/0251455 A1 | 11/2005 | Boesen |
| 2005/0266876 A1 | 12/2005 | Boesen |
| 2006/0029246 A1 | 2/2006 | Boesen |
| 2006/0074671 A1 | 4/2006 | Farmaner et al. |
| 2006/0074808 A1 | 4/2006 | Boesen |
| 2008/0254780 A1 | 10/2008 | Kuhl et al. |
| 2009/0073070 A1 | 3/2009 | Rofougaran |
| 2010/0203831 A1 | 8/2010 | Muth |
| 2010/0285771 A1* | 11/2010 | Peabody ............... G08B 25/016 455/404.2 |
| 2016/0324478 A1* | 11/2016 | Goldstein ............... A61B 5/721 |

FOREIGN PATENT DOCUMENTS

| | | |
|---|---|---|
| JP | 06292195 | 10/1998 |
| WO | 2014043179 A2 | 3/2014 |
| WO | 2015110577 A1 | 7/2015 |
| WO | 2015110587 A1 | 7/2015 |

OTHER PUBLICATIONS

BRAGI is on Facebook (2014).
BRAGI Update—Arrival of Prototype Chassis Parts—More People—Awesomeness (May 13, 2014).
BRAGI Update—Chinese New Year, Design Verification, Charging Case, More People, Timeline(Mar. 6, 2015).
BRAGI Update—First Sleeves From Prototype Tool—Software Development Kit (Jun. 5, 2014).
BRAGI Update—Let's Get Ready to Rumble, a Lot to Be Done Over Christmas (Dec. 22, 2014).
BRAGI Update—Memories From April—Update on Progress (Sep. 16, 2014).
BRAGI Update—Memories from May—Update on Progress—Sweet (Oct. 13, 2014).
BRAGI Update—Memories From One Month Before Kickstarter—Update on Progress (Jul. 10, 2014).
BRAGI Update—Memories From the First Month of Kickstarter—Update on Progress (Aug. 1, 2014).
BRAGI Update—Memories From the Second Month of Kickstarter—Update on Progress (Aug. 22, 2014).
BRAGI Update—New People @BRAGI—Prototypes (Jun. 26, 2014).
BRAGI Update—Office Tour, Tour to China, Tour to CES (Dec. 11, 2014).
BRAGI Update—Status on Wireless, Bits and Pieces, Testing-Oh Yeah, Timeline(Apr. 24, 2015).
BRAGI Update—The App Preview, The Charger, The SDK, BRAGI Funding and Chinese New Year (Feb. 11, 2015).
BRAGI Update—What We Did Over Christmas, Las Vegas & CES (Jan. 19, 2014).
BRAGI Update—Years of Development, Moments of Utter Joy and Finishing What We Started(Jun. 5, 2015).

(56) References Cited

OTHER PUBLICATIONS

BRAGI Update-Alpha 5 and Back to China, Backer Day, on Track(May 16, 2015).
BRAGI Update—Beta2 Production and Factory Line(Aug. 20, 2015).
BRAGI Update—Certifications, Production, Ramping Up.
BRAGI Update—Developer Units Shipping and Status(Oct. 5, 2015).
BRAGI Update—Developer Units Started Shipping and Status (Oct. 19, 2015).
BRAGI Update—Developer Units, Investment, Story and Status(Nov. 2, 2015).
BRAGI Update—Getting Close(Aug. 6, 2014).
BRAGI Update—On Track, Design Verification, How It Works and What's Next(Jul. 15, 2015).
BRAGI Update—On Track, On Track and Gems Overview.
BRAGI Update—Status on Wireless, Supply, Timeline and Open House@BRAGI(Apr. 1, 2015).
BRAGI Update—Unpacking Video, Reviews On Audio Perform and Boy Are We Getting Close(Sep. 10, 2015).
Farr, Christina: "iPads in Every Hospital: Apple's Plan to Crack the $3 Trillion Health Care Sector", "https://www.fastcompany.com/3069060/artists-and-scientists-are-teaming-with-businesses-and-non-profits-on-gender-concerns" (Mar. 18, 2017).
International Search Report & Written Opinion, PCT/EP2016/07216 (Oct. 18, 2016).
Last Push Before The Kickstarter Campaign Ends on Monday 4pm CET (Mar. 28, 2014).
Staab, Wayne J., et al., "A One-Size Disposable Hearing Aid is Introduced", The Hearing Journal 53(4):36-41) Apr. 2000.
Stretchgoal—It's Your Dash (Feb. 14, 2014).
Stretchgoal—The Carrying Case for the Dash (Feb. 12, 2014).
Stretchgoal—Windows Phone Support (Feb. 17, 2014).
The Dash + The Charging Case & The BRAGI News (Feb. 21, 2014).
The Dash-A Word From Our Software, Mechanical and Acoustics Team + An Update (Mar. 11, 2014).
Update From BRAGI—$3,000,000—Yipee (Mar. 22, 2014).

* cited by examiner

EARPIECE LIFE MONITOR WITH CAPABILITY OF AUTOMATIC NOTIFICATION SYSTEM AND METHOD

PRIORITY STATEMENT

This application claims priority to U.S. Provisional Patent Application 62/312,139, filed on Mar. 23, 2016, and entitled Earpiece Life Monitor with Capability of Automatic Notification System and Method, hereby incorporated by reference in its entirety.

FIELD OF THE INVENTION

The present invention relates to wearable devices. More particularly, but not exclusively, the present invention relates to ear pieces.

BACKGROUND

Individuals with chronic debilitating conditions oftentimes face extreme challenges when attempting to live independent lives without significant oversight. Such individuals are frequently presented with challenges that the average able bodied individual cannot comprehend. These include many of the activities of daily living, i.e. bathing, eating and unassisted ambulation throughout their dwelling. While the fully ambulatory individual would not consider these tasks as posing any type of challenge, others are not so lucky. Consequently, there exists a need for a new device that can monitor the biometric levels of the user, communicate data directly to the user, contact secondary care providers or relatives, upload data from the user to a database, alert appropriate personnel in case of sensor data detection of a crisis level event, link to appropriate electronic data systems when emergency medical responders to transfer data regarding the event, and allow the device to access the phone network through voice interfaces so that an incapacitated user would be able to place the phone call directly from their position after the event occurrence.

Therefore, what is needed is an improve ear piece which includes a life monitor.

SUMMARY

Therefore, it is a primary object, feature, or advantage of the present invention to improve over the state of the art.

It is a further object, feature, or advantage of the present invention to provide an earpiece which can monitor the biometric levels of the user.

It is a still further object, feature, or advantage of the present invention to provide an earpiece that can communicate data directly to the user.

Another object, feature, or advantage is to provide an earpiece which can contact secondary care providers or relatives.

Yet another object, feature, or advantage is to provide an earpiece which can upload data from the user to a database or remote server.

A further object, feature, or advantage is to alert appropriate personnel in case sensor data detection of a crisis level event.

A still further object, feature, or advantage is to link to appropriate electronic data systems with emergency medical responders to transfer data regarding an event.

Another object, feature, or advantage is to allow a device to access the phone network through voice interfaces so that an incapacitated user would be able to place a phone call directly from their position after an occurrence of an emergency or crisis level event.

One or more of these and/or other objects, features, or advantages of the present invention will become apparent from the specification and claims that follow. No single embodiment need provide each and every object, feature, or advantage. Different embodiments may have different objects, features, or advantages. Therefore, the present invention is not to be limited to or by an objects, features, or advantages stated herein.

According to one aspect methods and systems for the ongoing monitoring and care of the person suffering from incapacitation are provided. This may be used in settings ranging from in-hospital care and monitoring of the individual in each hospital bed or room to the individual who has been released from the facility to continue their lives in the at-home situation. This new construct may effectively solve the issues currently facing individuals recovering from recent interventions through individuals forced to live with ongoing issues that affect their ability to perform the activities of daily living in their home environments. The in-ear solution provides a robust platform to provide superior service to these individuals and allow them the comfort, safety and enhanced security of an effective biometric monitor and warning system.

According to another aspect, an earpiece includes an earpiece housing, at least one biometric sensor disposed within the earpiece, a wireless transceiver disposed within the earpiece for voice communications, a processor operatively connected to the at least one biometric sensor and the wireless transceiver, a speaker operatively connected to the processor, and at least one microphone operatively connected to the processor. The earpiece is configured to monitor biometrics of a user using the at least one biometric sensor, communicate biometric data to the user, detect a crisis level event, and communicate occurrence of the crisis level event using the wireless transceiver. The earpiece may be further configured to upload the biometric data to a database associated with a remote server. The earpiece may be configured to communicate the biometric data to the user through voice feedback. The earpiece may be configured to communicate the biometric data to the user by interacting with a mobile device in operative communication with the earpiece, the mobile device having a display so as to display the biometric data on the display of the mobile device. The earpiece may be configured to communicate occurrence of the crisis level event by initiating a voice call to a third party. The earpiece may be configured to communicate occurrence of the crisis level event by sending an indicator of the crisis level event to a remote server.

According to another aspect, a method for monitoring an individual suffering from at least partial incapacitation is provided. The method includes providing an earpiece comprising an earpiece housing, at least one biometric sensor disposed within the earpiece, a wireless transceiver disposed within the earpiece for voice communications, a processor operatively connected to the at least one biometric sensor and the wireless transceiver, a speaker operatively connected to the processor, and at least one microphone operatively connected to the processor. The method further includes monitoring biometrics of a user of the earpiece using the at least one biometric sensor, detecting a crisis level event using the biometrics, and wirelessly communicating an alert associated with the crisis level event from the earpiece to a remote location using the wireless transceiver. The method may further include communicating the biometrics of the user of the earpiece to the user. The communicating of the biometrics may include the step of generating speech describing the biometrics of the user of earpiece at a speaker of the earpiece. The communicating of the biometrics may include communicating the biometric data to the user by interacting with a mobile device in operative communication with the earpiece, the mobile device having a display so as to display the biometric data on the display of the mobile device. The step of wirelessly communicating the alert associated with the crisis level event from the earpiece to the remote location using the wireless transceiver may include accessing a mobile device in operative communication with the earpiece and initiating a voice call using the mobile device.

According to another aspect, a system includes an earpiece comprising (a) an earpiece housing, (b) at least one biometric sensor disposed within the earpiece, (c) a wireless transceiver disposed within the earpiece for voice communications, (d) a processor operatively connected to the at least one biometric sensor and the wireless transceiver, (e) a speaker operatively connected to the processor, and (f) at least one microphone operatively connected to the processor. The system may further include a software application executing on a mobile device in operative communication with the earpiece. The earpiece may be configured to monitor biometrics of a user using the at least one biometric sensor, communicate biometric data to the software application executing on the mobile device. The earpiece may be configured to detect a crisis level event by analyzing the biometric data. The earpiece may be configured to communicate occurrence of the crisis level to the mobile device.

DETAILED DESCRIPTION

The present invention is some aspects provides for the ongoing monitoring and care of a person suffering from incapacitation. This may be used in a variety of different settings including in-hospital care and monitoring of each individual in each hospital bed or room to the individual who has been released from the facility to continue their lives in the at-home situation. This new construct may effectively solve the issues currently facing individuals recovering from recent interventions through individuals forced to live with ongoing issues that affect their ability to perform the activities of daily living in their home environments. The in-ear solution provides a robust platform to provide superior service to these individuals and allow them the comfort, safety and enhanced security of an effective biometric monitor and warning system.

Figure 1:
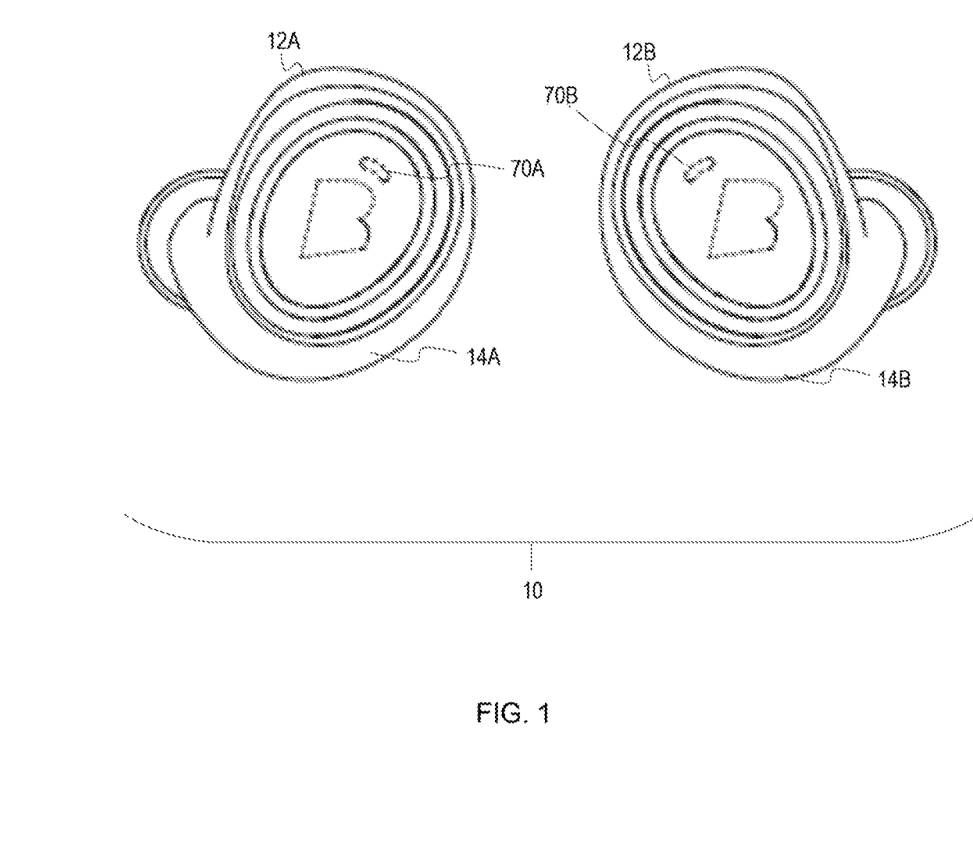
FIG. 1 illustrates a set of earpieces including a left earpiece and a right earpiece.

FIG. 1 illustrates a set of earpieces 10 including a left earpiece 12A and a right earpiece 12B. The left earpiece 12A has a housing or casing 14A and the right earpiece 12B has a housing or casing 14B. A microphone 70A is shown on the left earpiece 12A and a microphone 70B is shown on the right earpiece 12B.

Figure 2:
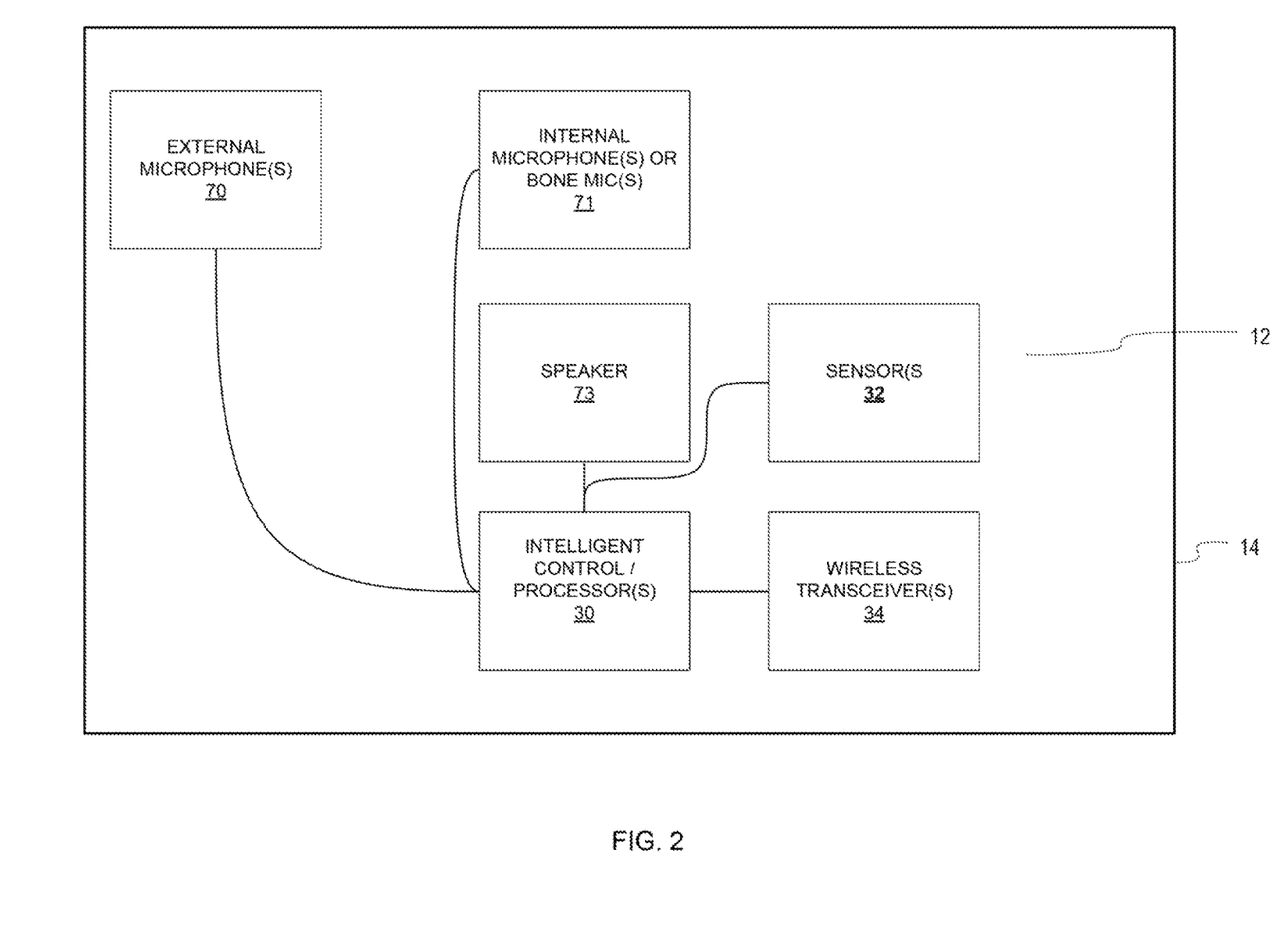
FIG. 2 is a block diagram of one example of an earpiece.

FIG. 2 illustrates an earpiece 12 which ma be a left earpiece or a right earpiece. One or more processors or other intelligent control 30 are shown disposed within the housing 14 of the earpiece. One or more wireless transceivers 34 are operatively connected to the intelligent controls 30. The term "processor" as used herein means a single processor or more than one processor in operative communication. The processor or intelligent control 30 may include a digital signal processor, a microprocessor, both, and/or other types of processors. The wireless transceivers 34 may include a BLUETOOTH transceiver, an ultra-wideband (UWB) transceiver, or type of radio transceiver, a near field magnetic induction (NFMI) transceiver, or other type of transceiver. One or more external microphones 70 is/are operatively connected to the processor 30 as are one or more internal microphones or bone microphones 71. One or more sensors 32, including biological or physiological or other biometric sensors may be operatively connected to the processor 30.

Figure 3:
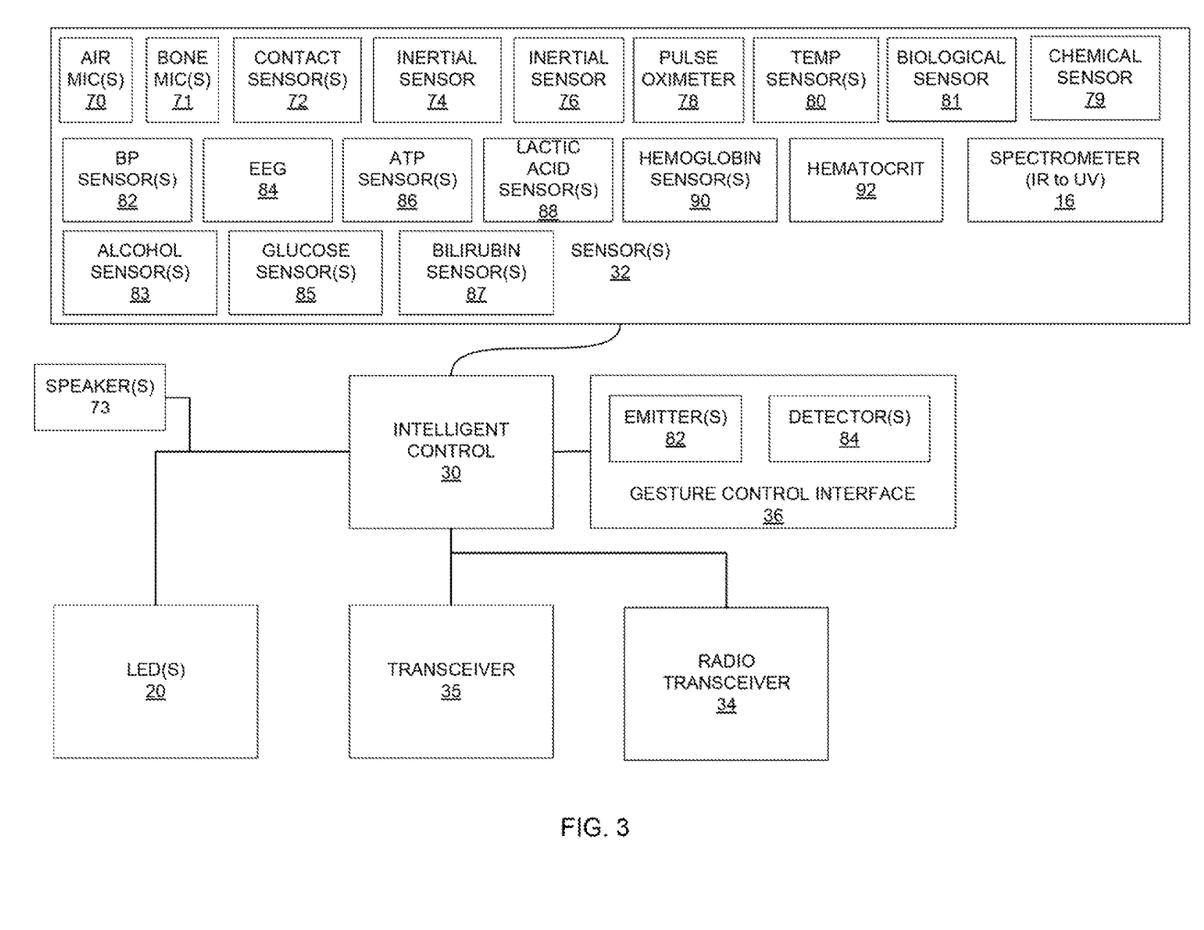
FIG. 3 is a block diagram of another example of an earpiece.

FIG. 3 is a block diagram illustrating a device. The device may include one or more LEDs 20 electrically connected to an intelligent control 30. The intelligent control system 30 may include one or more processors, microcontrollers, application specific integrated circuits, or other types of integrated circuits. The intelligent control 30 may also be electrically connected to one or more sensors 32. Where the device is an earpiece, the sensor(s) may include an inertial sensor 74 and another inertial sensor 76. Each inertial sensor 74, 76 may include an accelerometer, a gyro, sensor or gyrometer, a magnetometer or other type of inertial sensor. The sensor(s) 32 may also include one or more contact sensors 72, one or more bone conduction microphones 71, one or more air conduction microphones 70, one or more chemical sensors 79, a pulse oximeter 76, a temperature sensor 80, or other physiological or biological sensor(s). Further examples of physiological or biological sensors include an alcohol sensor 83, glucose sensor 85, or bilirubin sensor 87. Other examples of physiological or biological sensors may also be included in the device. These may include a blood pressure sensor 82, an electroencephalogram (EEG) 84, an Adenosine Triphosphate (ATP) sensor, a lactic acid sensor 88, a hemoglobin sensor 90, a hematocrit sensor 92 or other biological or chemical sensor.

A spectrometer 16 is also shown. The spectrometer 16 may be an infrared (IR) through ultraviolet (UV) spectrometer although it is contemplated that any number of wavelengths in the infrared, visible, or ultraviolet spectrums may be detected. The spectrometer 16 is preferably adapted to measure environmental wavelengths for analysis and recommendations and thus preferably is located on or at the external facing side of the device.

A gesture control interface 36 is also operatively connected to or integrated into the intelligent control system 30. The gesture control interface 36 may include one or more emitters 82 and one or more detectors 84 for sensing user gestures. The emitters may be of any number of types including infrared LEDs. It is contemplated that instead of being light based, the gesture control interface 36 may be capacitance based instead. The device may include a transceiver 35 which may allow for induction transmissions such as through near field magnetic induction. A short range transceiver 34 using Bluetooth, BLE, UWB, or other means of radio communication may also be present. The short range transceiver 34 may be used to communicate with the vehicle control system. In operation, the intelligent control 30 may be configured to convey different information using one or more of the LED(s) 20 based on context or mode of operation of the device. The various sensors 32, the intelligent control 30, and other electronic components may be located on the printed circuit board of the device. One or more speakers 73 may also be operatively connected to the intelligent control 30.

A magnetic induction electric conduction electromagnetic (E/M) field transceiver 37 or other type of electromagnetic field receiver is also operatively connected to the intelligent control system 30 to link the processor 30 to the electromagnetic field of the user. The use of the E/M transceiver 37 allows the device to link electromagnetically into a personal area network or body area network or other device. Although various types of biometric sensors are shown and described, it is contemplated that one or more other sensors may be present. It is to be understood that any number of biometric sensors may be present including fewer or more than what is shown in FIG. 3. It is further contemplated that where multiple earpieces are used, a first or left earpiece may include a first subset of the sensors 32 and a second or right earpiece may include a second subset of the sensors 32.

Figure 4:
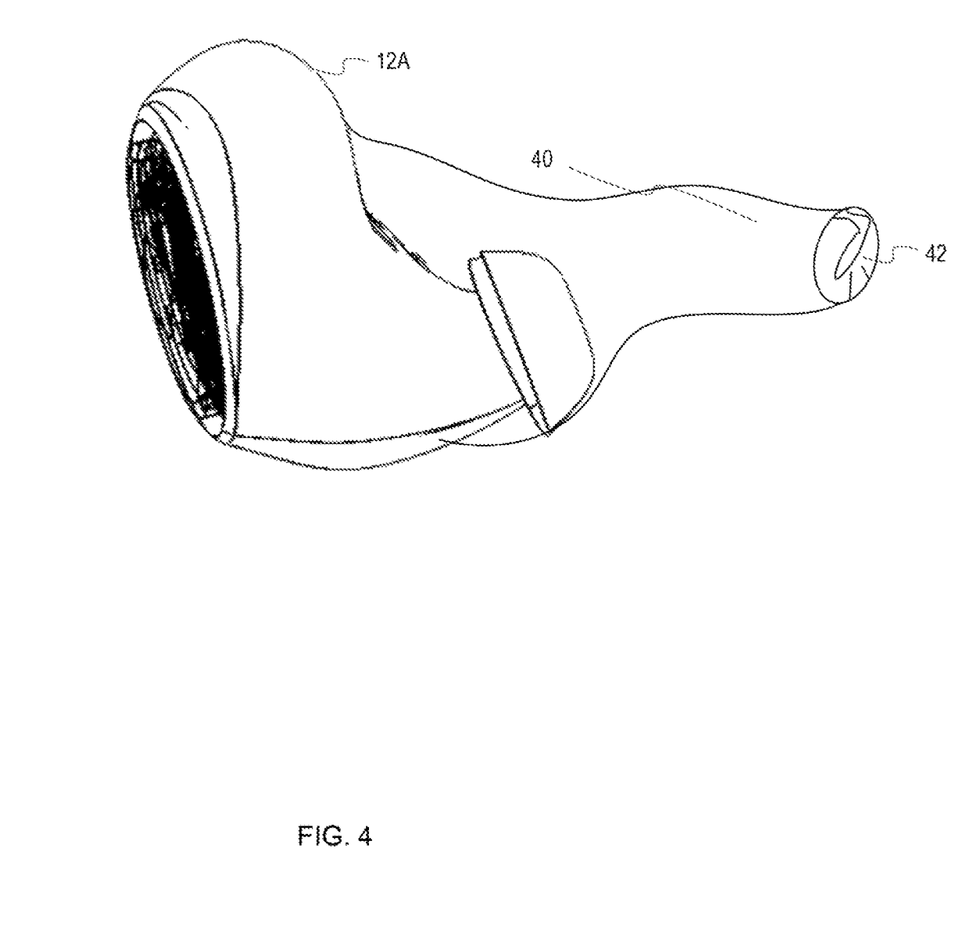
FIG. 4 illustrates one example of an earpiece fitted to an external auditory canal of a user.

FIG. 4 illustrates one example of an earpiece 12A positioned within an external auditory canal of a user. A tympanic membrane 42 is shown at the inner end of the external auditory canal 40. The earpiece may be used to perform any number of different types of sensing at or proximate to the ear of a user.

Figure 5:
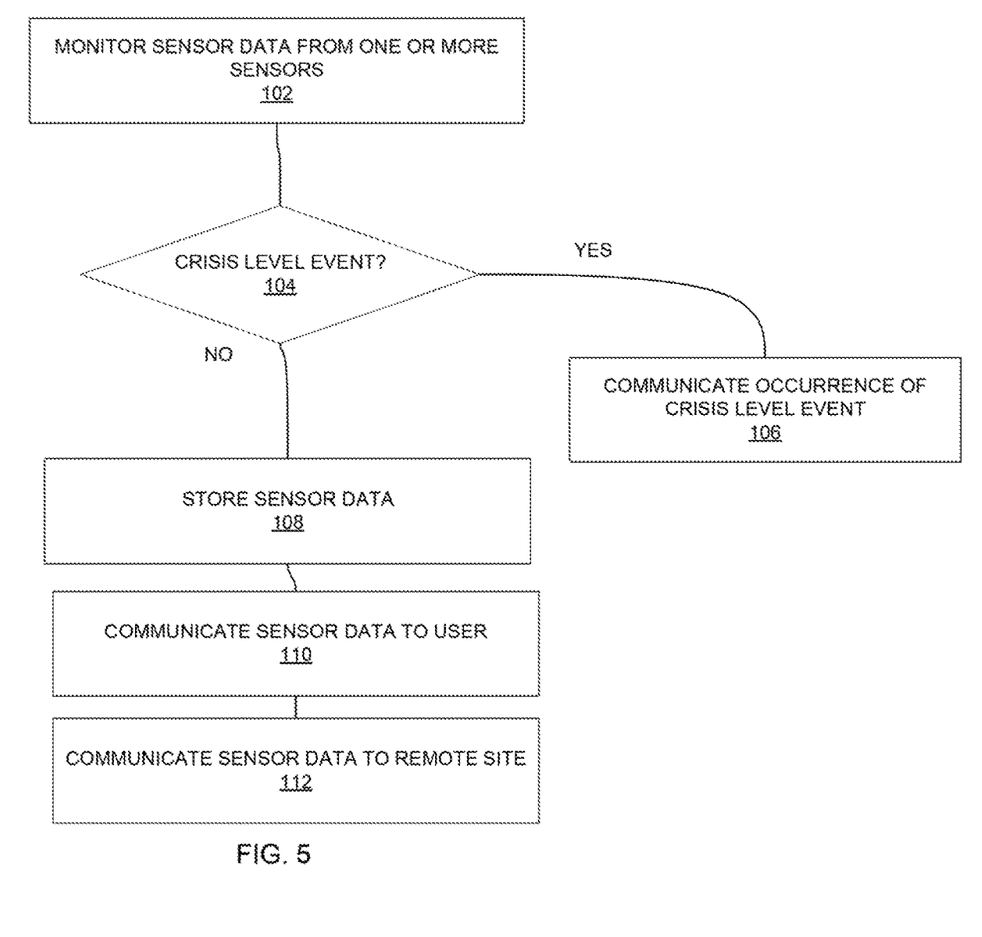
FIG. 5 is a flow diagram illustrating one example of a methodology.

FIG. 5 illustrated on example of a methodology according to another aspect. In step 102 sensor data from one or more sensors of one or more earpieces is monitored. In step 104 a determination may be made such as by the intelligent control system 30 of the earpiece as to whether or not a crisis level event has occurred. This determination may be performed in various ways. In one example, the determination is made by comparing a sensor reading to a threshold level associated with a crisis level event. If the sensor level crosses the threshold level than the device determines that a crisis level event has occurred.

In another example, a determination that a crisis level event has occurred only happens when the sensor readings cross the threshold for a particular number of consecutive readings or for a particular amount of time. Determining the occurrence of a crisis level event in this manner reduces likelihood of falsely identifying an event as a crisis level event.

Regardless of the manner in which the determination is made, if there is a crisis level event, then in step 106 the occurrence of the crisis level event may be communicated to the user, to emergency contacts, to emergency personnel, or others. If there is no crisis level event then in normal operation, the sensor data may be stored in step 108, the sensor data may communicated to a user in step 110, and the sensor data may be communicated to a remote site in step 112. These steps may occur in various ways. For example, the earpiece may be configured to upload the biometric data to a database associated with a remote server. In addition, the earpiece may be configured to communicate the biometric data to a user in any number of ways. For example, the earpiece may be configured to communicate the biometric data to the user through voice feedback. Thus, for example, when prompted by the user, periodically according to user preferences, or when a particular threshold is crossed, the earpiece may perform speech processing and speak the relevant data such as heat rate, glucose level, temperature, etc. Alternatively, the one or more earpieces may interact with a mobile device in operative communication therewith. The display of the mobile device may be used as a display to display biometric data collected from the earpiece. It should be understood that the mobile device may be a mobile device of a person wearing the earpiece or may be a different mobile device. Thus, for example, a patient who checks into a hospital may be assigned one or more earpieces to wear and a mobile device such as a tablet computer. The earpieces may communicate with the tablet computer which may be in operative communication with other hospital systems.

Returning to step 106, the occurrence of the crisis level event may be communicated to the user, to emergency contacts, to emergency personnel, or others. This may occur in various ways. For example, the earpiece may initiate a voice call to a third party. For example, the earpiece may be in operative communication with a mobile device such as a smart phone and initiate a voice call to a third party such as an emergency contact of the individual wearing the earpiece, an emergency service such as 911, a private health monitoring company, a nurse's station, a health care provider, or other individual. The person being monitored may then communicate with the third party. Thus, for example, third party may then ask the person being monitored if they are all right or ask them for relevant information. If data is being logged to a remote site that the third party has access to, the third party may then check the data on the remote site to provide them with additional information regarding the situation. The earpiece may also provide for speech processing to communicate the alert verbally to the third party which may be useful if the person being monitored is non-verbal or unable to respond. The earpiece may also directly prompt the user if they are all right such as providing a voice prompt and asking the user to respond using voice or respond by using the gestural interface of the earpiece and tap, double tap, triple tap, swipe, or otherwise provide user input to the earpiece.

The third party may be notified in other ways as well. For example, wherein the earpiece is configured to communicate occurrence of the crisis level event by sending an indicator of the crisis level event to a remote server. The remote server may then make a phone call, send a text message, send an email, send a social media or application specific notification, or otherwise provide a notification or alert.

It should also be understood that the earpiece may include an earpiece identifier which identifies the earpiece and/or the person wearing the earpiece. Thus, an identity of the person wearing the earpiece may also be communicated along with the sensor data.

Therefore, various methods, systems, and apparatus have been shown and described. The present invention contemplates numerous options, variation, and alternatives and is not to be limited to the specific embodiments shown herein.

What is claimed is:

1. A set of wireless earpieces comprising a first wireless earpiece and a second wireless earpiece:
  the first wireless earpiece comprising:
    an earpiece housing;
    at least one biometric sensor disposed within the first wireless earpiece;
    a wireless radio transceiver disposed within the first wireless earpiece for voice communications;
    an intelligent control, disposed within the first wireless earpiece, operatively connected to the at least one biometric sensor and the wireless radio transceiver;
    a near field magnetic induction transceiver operatively connected to the intelligent control for operative communication with the second wireless earpiece;
    a speaker operatively connected to the intelligent control;

an inertial sensor operatively connected to the intelligent control;
at least one microphone operatively connected to the intelligent control;
the second wireless earpiece comprising:
at least one biometric sensor disposed within the second earpiece;
an intelligent control within the second wireless earpiece and operatively connected to the at least one biometric sensor;
a near field magnetic induction transceiver operatively connected to the intelligent control for operative communication with the first wireless earpiece;
a speaker operatively connected to the intelligent control;
an inertial sensor operatively connected to the intelligent control;
at least one microphone operatively connected to the intelligent control;
wherein the set of wireless earpieces is configured to monitor biometrics of a user using the at least one biometric sensor of the first wireless earpiece and the at least one biometric sensor of the second wireless earpiece to provide biometric data, monitor inertial changes of the user using the inertial sensor of the first wireless earpiece and the inertial sensor of the second wireless earpiece, communicate the biometric data and the inertial data to the user, detect a crisis level event, and communicate occurrence of the crisis level event to a remote location using the wireless radio transceiver;
wherein the set of wireless earpieces is configured to provide a direct voice prompt from the set of wireless earpieces to the user upon detecting a crisis level event, requesting the user to provide user input comprising a gesture.

2. The set of wireless earpieces of claim 1 wherein the set of wireless earpieces is further configured to upload the biometric data to a database associated with a remote server.

3. The set of wireless earpieces of claim 1 wherein the set of wireless earpieces is configured to communicate the biometric data to the user through voice feedback.

4. The set of wireless earpieces of claim 1 wherein the set of wireless earpieces is configured to communicate occurrence of the crisis level event by initiating a voice call to a third party.

5. The set of wireless earpieces of claim 1 wherein the set of wireless earpieces is configured to communicate occurrence of the crisis level event by initiating a voice call to a third party.

6. The set of wireless earpieces of claim 1 wherein the set of wireless earpieces is configured to communicate occurrence of the crisis level event by sending an indicator of the crisis level event to a remote server.

7. A method for monitoring an individual suffering from at least partial incapacitation, the method comprising steps of:
assigning a set of wireless earpieces to an individual once the individual is admitted to a health care facility;
wherein the set of wireless earpieces includes a first earpiece and a second earpiece; the first earpiece comprising a first earpiece housing, at least one biometric sensor disposed within the first earpiece housing, a wireless radio transceiver disposed within the first earpiece housing for voice communications, an intelligent control operatively connected to the at least one biometric sensor and the wireless radio transceiver, a speaker operatively connected to the intelligent control, and at least one microphone operatively connected to the intelligent control, an inertial sensor operatively connected to the intelligent control, and a near field magnetic induction transceiver operatively connected to the intelligent control for communication with the second earpiece;
wherein the second earpiece comprises a second earpiece housing, at least one biometric sensor disposed within the second earpiece housing, a speaker, at least one microphone, an intelligent control operatively connected to the at least one biometric sensor, to the speaker and the at least one microphone, an inertial sensor operatively connected to the intelligent control and a near field magnetic induction transceiver operatively connected to the intelligent control for communication with the first earpiece;
monitoring biometric data and inertial data of a user of the set of wireless earpieces using the at least one biometric sensor of the first earpiece, the at least one biometric sensor of the second earpiece, the inertial sensor of the first earpiece and an inertial sensor of the second earpiece;
detecting a crisis level event using the biometric data and the inertial data;
confirming the crisis level event by providing a direct voice prompt from the set of wireless earpieces requesting the user to provide user input comprising a gesture; and
wirelessly communicating an alert associated with the crisis level event from the set of wireless earpieces to a remote location using the wireless radio transceiver of the first earpiece.

8. The method of claim 7 further comprising communicating the biometric data of the user of the set of wireless earpieces to the user.

9. The method of claim 8 wherein the communicating the biometric data of the user of the set of wireless earpieces to the user comprises generating speech describing the biometric data of the user of the set of wireless earpieces at a speaker of the set of wireless earpieces.

10. The method of claim 9 wherein the communicating the biometric data of the user of the set of wireless earpieces to the user comprises communicating the biometric data to the user by interacting with a mobile device in operative communication with the set of wireless earpieces, the mobile device having a display so as to display the biometric data on the display of the mobile device.

11. The method of claim 10 wherein the mobile device is a tablet computer.

12. The method of claim 7 wherein the wirelessly communicating the alert associated with the crisis level event from the set of wireless earpieces to the remote location using the wireless radio transceiver comprises accessing a mobile device in operative communication with the earpiece and initiating a voice call using the mobile device.

13. The method of claim 7 wherein the step of detecting the crisis level further comprises at least one of crossing a predetermined threshold a preset number of consecutive sensor readings and crossing a predetermined threshold for a preset amount time.

14. The method of claim 7 wherein the first earpiece further comprises a gestural interface operatively connected to the intelligent control of the first earpiece.

15. A system comprising:
a set of wireless earpieces comprising of a first wireless earpiece and a second wireless earpiece;

the first wireless earpiece comprising (a) an earpiece housing, (b) at least one biometric sensor disposed within the first wireless earpiece, (c) a wireless radio transceiver disposed within the first wireless earpiece for voice communications, (d) an intelligent control operatively connected to the at least one biometric sensor and the wireless radio transceiver, (e) a speaker operatively connected to the intelligent control, (f) at least one microphone operatively connected to the intelligent control, (g) an inertial sensor operatively connected to the intelligent control and (h) a near field magnetic induction transceiver operatively connected to the intelligent control for communication with the second earpiece;

the second wireless earpiece comprising: (a) an earpiece housing, (b) at least one biometric sensor disposed within the second earpiece, (c) an intelligent control operatively connected to the at least one biometric sensor, (d) a speaker operatively connected to the intelligent control, (e) at least one microphone operatively connected to the intelligent control, (f) an inertial sensor operatively connected to the intelligent control and (g) a near field magnetic transceiver operatively connected to the intelligent control for communication with the second earpiece;

a software application executing on a mobile device in operative communication with the set of wireless earpieces;

wherein the set of wireless earpieces is configured to monitor biometric data of a user using the at least one biometric sensor of the first wireless earpiece and the at least one biometric sensor of the second wireless earpiece, monitor inertial data of the user using the inertial sensor of the first wireless earpiece and the inertial sensor of the second wireless earpiece, and communicate the biometric data and the inertial data to the software application executing on the mobile device;

wherein the set of wireless earpieces is configured to detect a crisis level event by analyzing the biometric data and the inertial data;

wherein the set of wireless earpieces is configured to confirm the crisis level event by providing a direct voice prompt from the set of wireless earpieces requesting the user to provide user input comprising a gesture to the set of wireless earpieces;

wherein the set of wireless earpieces is further configured to communicate occurrence of the crisis level to the mobile device.

16. The system of claim 15 wherein the mobile device is a tablet computer.

17. The system of claim 15 wherein the mobile device is a phone.

* * * * *